United States Patent [19]

Sugimori et al.

[11] Patent Number: 4,487,954
[45] Date of Patent: Dec. 11, 1984

[54] CARBOXYLIC ACID CYCLOHEXYL ESTER DERIVATIVES

[75] Inventors: Shigeru Sugimori; Tetsuhiko Kojima; Masakazu Tsuji, all of Kanagawaken, Japan

[73] Assignee: Chisso Corporation, Osaka, Japan

[21] Appl. No.: 303,523

[22] Filed: Sep. 17, 1981

[30] Foreign Application Priority Data

| Sep. 19, 1980 | [JP] | Japan | 55-130331 |
|---|---|---|---|
| Oct. 14, 1980 | [JP] | Japan | 55-143393 |
| Oct. 21, 1980 | [JP] | Japan | 55-147109 |
| Mar. 28, 1981 | [JP] | Japan | 56-46064 |
| Apr. 7, 1981 | [JP] | Japan | 56-52198 |
| Apr. 16, 1981 | [JP] | Japan | 56-57380 |
| Jun. 10, 1981 | [JP] | Japan | 56-89390 |
| Jun. 18, 1981 | [JP] | Japan | 56-94380 |

[51] Int. Cl.$^3$ .......................................... C07C 69/76
[52] U.S. Cl. ........................................ 560/107; 560/1; 560/65; 560/73; 560/106; 560/118; 560/126; 260/463; 260/465 D; 260/410.5; 260/410; 252/299.63
[58] Field of Search ............ 560/73, 107, 118, 1, 560/65, 106, 126; 260/463, 410.5, 410; 252/299.63

[56] References Cited

U.S. PATENT DOCUMENTS

| 4,228,029 | 10/1980 | Osman | 560/73 |
|---|---|---|---|
| 4,229,315 | 10/1980 | Krause et al. | 560/73 |
| 4,293,434 | 10/1981 | Deutscher | 560/73 |

FOREIGN PATENT DOCUMENTS 4148184 11/1979 Japan .................. 252/299.63

OTHER PUBLICATIONS

Mol. Cryst. Liq. Cryst., 1976, vol. 37, pp. 157, 158, 168 & 175.

*Primary Examiner*—Paul J. Killos
*Attorney, Agent, or Firm*—Wenderoth, Lind & Ponack

[57] ABSTRACT

Liquid crystal compounds useful as a component of liquid crystal compositions having superior actuation characteristics within a broader temperature range are provided, which compounds are carboxylic acid cyclohexyl ester derivatives expressed by the general formula $$A-\underset{\underset{O}{\|}}{C}-O-\text{[cyclohexyl]}-B \quad (I)$$

wherein
A represents

[structures: F-phenyl-, Cl-phenyl-, F,F-phenyl-, Cl,Cl-phenyl-, NC-phenyl-, R-cyclohexyl-, R-bicyclohexyl-, R-phenyl-, R-cyclohexyl-phenyl-, RO-phenyl-]

R- or RO-;
B represents

[structures: cyclohexyl-R' or phenyl-R']

R represents an alkyl group or an alkoxy group, both having 1 to 10 carbon atoms; and R' represents an alkyl group having 1 to 10 carbon atoms.

6 Claims, No Drawings

CARBOXYLIC ACID CYCLOHEXYL ESTER DERIVATIVES

BACKGROUND OF THE INVENTION

This invention relates to novel ester compounds exhibiting a liquid crystal phase within a broader temperature range.

Liquid crystal elements utilize optical anisotropy and dielectric anisotropy of liquid crystal substances and are classified by their display modes into various types such as TN type (twisted nematic type), DS type (dynamic scattering type), guest-host type, DAP type, etc.; and the properties of liquid crystal substances suitable to their respective uses are different. However, it is common to any of such liquid crystal substances that they must be stable to moisture, air, heat, light, etc., and also they must exhibit a liquid crystal phase within as broad a temperature range as possible, centering about room temperature, and further have an optimum dielectric anisotropy value ($\Delta\epsilon$) which is varied depending on the kinds of the display elements. However, no single compounds satisfying such requirements has been found to date, and it is the present status that liquid crystal compositions obtained by mixing together several kinds of liquid crystal compounds and non-liquid crystal compounds have been used. Recently, in particular, liquid crystal display elements actuated within a temperature range from about $-20°$ C. to about $80°$–$90°$ C. have come to be required. Thus, liquid crystal compositions having superior actuation characteristics within a broader temperature range have been desired.

The object of the present invention is to provide novel liquid crystal compounds useful as a component of such liquid crystal compositions.

SUMMARY OF THE INVENTION

The present invention resides in:

Carboxylic acid cyclohexyl ester derivatives expressed by the general formula

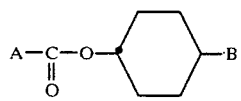

(I)

wherein
A represents

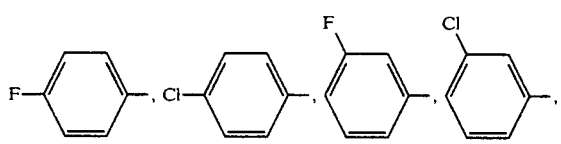

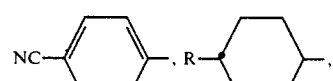

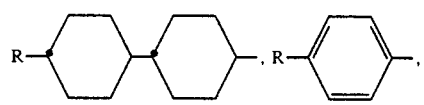

R- or RO-; B represents

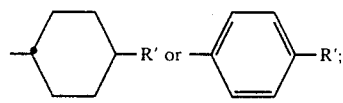

R represents an alkyl group or an alkoxy group, both having 1 to 10 carbon atoms; and R' represents an alkyl group having 1 to 10 carbon atoms.

DESCRIPTION OF PREFERRED EMBODIMENTS

The following compounds having a formula of (II) to (VI), included among those of the formula (I), exhibit a not so large positive dielectric anisotropy value ($\Delta\epsilon$: about $+0.2$ to $+5$); have a broader nematic temperature range; in particular have a higher transparent point (N-I point); on the other hand, also have a property of reducing the viscosity of liquid crystal compositions; and can improve actuation characteristics at lower temperatures. Thus they are very useful for obtaining liquid crystal compositions having a broader liquid crystal temperature range.

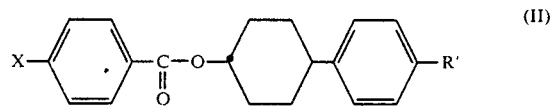

(II)

wherein X represents F or Cl and R' represents an alkyl group of 1 to 10 carbon atoms;

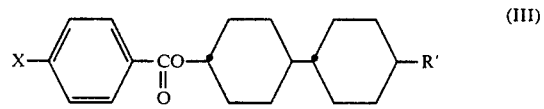

(III)

wherein X represents F or Cl and R' represents an alkyl group of 1 to 10 carbon atoms;

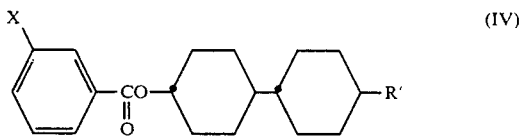

(IV)

wherein X represents F or Cl and R' represents an alkyl group of 1 to 10 carbon atoms;

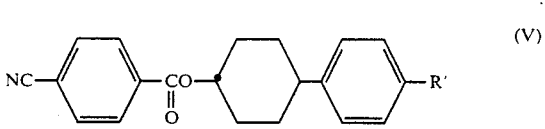

(V)

wherein R' represents an alkyl group of 1 to 10 carbon atoms; and

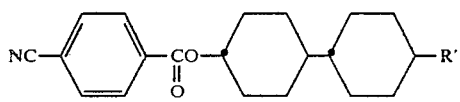

wherein R' represents an alkyl group of 1 to 10 carbon atoms.

Further, the following compounds having a formula of (VII) to (X), included among those of the formula (I), exhibit a liquid crystal phase within a broader temperature range and in particular have a higher transparent point; hence they are useful for extending the actuation temperature range of liquid crystal compositions toward the higher temperature side.

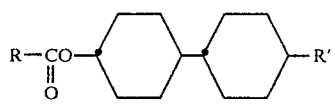

wherein R represents an alkyl group or an alkoxy group, both having 1 to 10 carbon atoms, and R' represents an alkyl group of 1 to 10 carbon atoms;

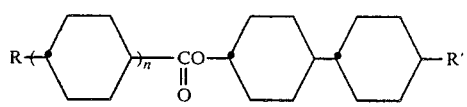

wherein R and R' both represent an alkyl group of 1 to 10 carbon atoms and n represents 1 or 2;

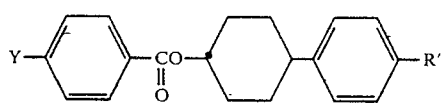

wherein Y represents R, RO or

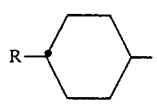

and R and R' both represent an alkyl group of 1 to 10 carbon atoms; and

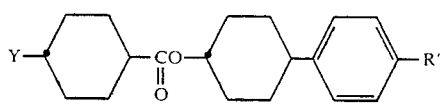

wherein Y represents R or

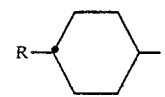

and R and R' both represent an alkyl group of 1 to 10 carbon atoms.

Next, the preparation of the compounds of the present invention will be described.

First the preparation of cyclohexanol derivatives will be mentioned.

A 4-alkyl-4'-hydroxybiphenyl is hydrogenated in ethanol in the presence of Raney nickel catalyst, followed by further reacting metallic sodium to obtain a trans-4-(4'-alkylphenyl)cyclohexanol.

Also, a 4-(trans-4'-alkylcyclohexyl)phenol is reduced in ethanol in the presence of Raney nickel catalyst, at 100° C. under 20 atms, followed by recrystallization and separation of trans-form from cis-form to obtain a trans-4-(trans-4'-alkylcyclohexyl)cyclohexanol.

The above reactions are expressed by the following equations:

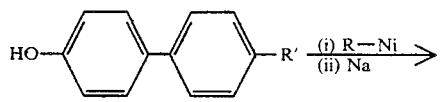

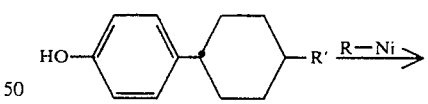

On the other hand, various carboxylic acids prepared in known manners are converted into acid chlorides with thionyl chloride. Such acid chlorides are then reacted with the cyclohexanol derivatives obtained above in the presence of pyridine to prepare cyclohexyl ester derivatives of carboxylic acids.

The above reactions are expressed by the following equations:

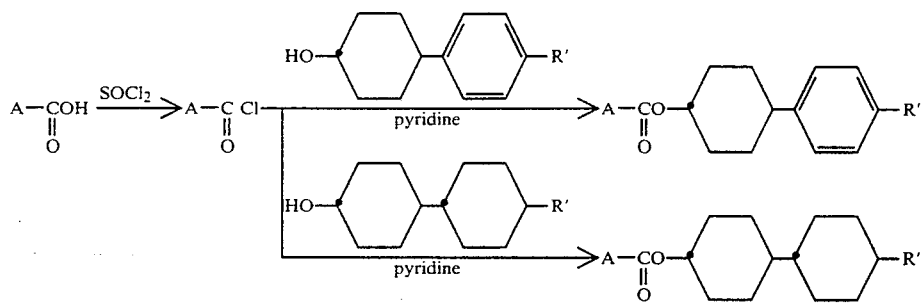

The following examples of preparation and use of the compounds of the present invention illustrate the invention in more detail.

EXAMPLE 1

Preparation of 4-fluorobenzoic acid trans-4'-(4''-heptylphenyl)cyclohexal ester (a compound of the formula (II) wherein X=F and R'=$C_7H_{15}$)

4-(4'-heptylphenyl)phenol (200 g) is dissolved in ethanol (0.5 l) and a commercially available Raney nickel (20 g) is added, followed by hydrogenation in an autoclave at 80° to 120° C. under a hydrogen pressure of 30 to 40 Kg/cm$^2$G. The reaction is traced by gas chromatography (column: SIDC-560-10%, 2 m, 280° C.) and is stopped when the raw material is extinct. The catalyst is filtered off from the hydrogenation product and ethanol is distilled off under reduced pressure, followed by dissolving the residue in toluene (200 ml). On the other hand, metallic sodium (18.4 g) is added to toluene (400 ml) and heated to 110° C., followed by quenching under a high speed agitation to prepare a sodium dispersion, which is then cooled down to room temperature, after which the above toluene solution of the hydrogenation product is added and the mixture is then agitated at room temperature for one hour. The resulting material is agitated at 100° C., for 4 hours, followed by cooling and then gradually adding methanol (200 ml). The whole is transferred into a separating funnel, followed by washings twice with 10% hydrochloric acid (200 ml) and once with a saturated aqueous solution of sodium hydrogen carbonate (200 ml) and repeated washings with water untill the water layer becomes neutral. The toluene layer is dried over anhydrous sodium sulfate, followed by distilling off toluene under reduced pressure, adding n-hexane (200 ml) and standing overnight to obtain crystals of trans-4-(4'-heptylphenyl)cyclohexanol. Yield: 41.6 g, 20.4%. M.p.: 80.2°–82.5° C.

Separately, thionyl chloride (5 ml) is added to 4-fluorobenzoic acid (1.2 g) and the mixture is warmed at 60° C. for 3 hours, followed by distilling off excess thionyl chloride under reduced pressure to obtain 4-fluorobenzoyl chloride. To this chloride is added a solution of trans-4-(4'-heptylphenyl)cyclohexanol obtained above (2 g) in pyridine (2 ml) and toluene (50 ml), followed by vigorous shaking. The resulting reaction liquid is allowed to stand at room temperature overnight, followed by pouring it into water (50 ml) and further adding toluene (50 ml) to carry out extraction. The toluene layer is washed with 6N hydrochloric acid and then with 2N aqueous solution of sodium hydroxide, followed by washing with water until the layer becomes neutral, drying over anhydrous sodium sulfate and distilling off toluene under reduced pressure. The residual oily substance is recrystallized from ethanol to obtain the objective 4-fluorobenzoic acid trans-4-(4''-heptylphenyl)cyclohexyl ester. Yield: 2.6 g, 90.0%, C-Sm: 62.0°–62.3° C., Sm-N point: 78.4° C., N-I point: 102.1°–102.7° C.

EXAMPLE 2-10

Other compounds of the formula (II) were prepared as in Example 1. Their yields, physical properties, etc. are shown together with the results of Example 1 in Table 1.

TABLE 1

| | In formula (II) | | Yield | | Phase transition points (°C.)* | |
|---|---|---|---|---|---|---|
| Example | X | R' | (g) | (%) | M.P. or C-N point | N-I point |
| 2 | F | $C_3H_7$ | 2.6 | 83.4 | 100.5~101.6 | 121.3~121.5 |
| 3 | F | $C_4H_9$ | 2.8 | 91.8 | 108.8~109.1 | 105.6 (monotropic) |
| 4 | F | $C_5H_{11}$ | 2.9 | 96.9 | 104.2~105.0 | 111.7~112.0 |
| 5 | F | $C_6H_{13}$ | 2.6 | 88.5 | 90.8~90.9 | 96.2~96.5 |
| 6 | Cl | $C_3H_7$ | 2.4 | 73.4 | 116.8~117.7 | 148.0~148.4 |
| 7 | Cl | $C_4H_9$ | 2.4 | 75.1 | 99.9~100.2 | 134.0~134.1 |
| 8 | Cl | $C_5H_{11}$ | 2.6 | 83.1 | 95.5~96.8 | 137.6~138.0 |
| 9 | Cl | $C_6H_{13}$ | 2.3 | 75.0 | 95.5~96.5 | 120.0~121.1 |
| 10 | Cl | $C_7H_{15}$ | 2.5 | 83.0 | 76.6~77.1 | 125.2~125.5 |
| 1 | F | $C_7H_{15}$ | 2.6 | 90.0 | 62.0~62.3 (C-Sm) 78.4 (Sm-N) | 102.1~102.7 |

*C: solid phase,
N: nematic phase,
I: transparent phase,
Sm: smectic phase

EXAMPLE 11

Preparation of 4-fluorobenzoic acid trans-4'-(trans-4''-pentylcyclohexyl)cyclohexyl ester (a compound of the formula (III) wherein X=F and R'=$C_5H_{11}$)

Ten % by weight (20 g) of Raney nickel was added to 4-(trans-4'-pentylcyclohexyl)phenol (200 g), and ethanol (1.8 l) was added to dissolve the phenol, followed by absorbing 3 mols of hydrogen based on one mol of the raw material phenol, into the solution at 100° C. under a hydrogen pressure of 20 Kg/cm$^2$G. After completion of the hydrogenation, the catalyst was filtered off and ethanol was vaporized to concentrate the solution so as to give a volume of about 0.3 l, followed by adding fresh ethanol, recrystallization and filtration to obtain trans-4-(trans-4'-pentylcyclohexyl)cyclohexanol (77 g) (yield: 37.6%).

M.p.: 121°–123° C.

On the other hand, 4-fluorobenzoic acid (0.01 mol) (1.4 g) was reacted with thionyl chloride (10 ml) at 60°

C. for 30 minutes and then at 80° C. for 2 hours to obtain a uniform solution, which was then allowed to stand for one hour, followed by distilling off excess thionyl chloride to obtain 4-fluorobenzoyl chloride as residue.

The total amount (0.01 mol) of this 4-fluorobenzoyl chloride was added to and reacted with a solution obtained by dissolving trans-4-(trans-4'-pentylcyclohexyl)cyclohexanol (2.5 g) (0.01 mol) obtained above, in

EXAMPLES 16-20

Using 3-halogenobenzoic acids in place of 4-halogenobenzoic acids in Examples 11-15, 3-halogenobenzoic acid trans-4'-(trans-4"-alkylcyclohexyl)cyclohexyl esters of the formula (IV) were similarly obtained. Their physical properties, etc. are shown in Table 3.

TABLE 3

| Example | In formula (IV) X | In formula (IV) R' | Amount of HO-⬡-⬡-R' used (g) | Yield (g) | Yield (%) | Phase transition points (°C.) C—Sm | Phase transition points (°C.) Sm—N | Phase transition points (°C.) N—I | | Elemental analysis values Analytical values | Elemental analysis values Calculated values |
|---|---|---|---|---|---|---|---|---|---|---|---|
| 16 | F | $C_3H_7$ | 2.2 | 1.5 | 43 | 66 | 72 | 135 | C | 76.5 | 76.3 |
|  |  |  |  |  |  |  |  |  | H | 9.1 | 9.0 |
| 17 | F | $C_4H_9$ | 2.4 | 1.6 | 44 | 42 | 55 | 125 | C | 76.4 | 76.6 |
|  |  |  |  |  |  |  |  |  | H | 9.2 | 9.2 |
| 18 | F | $C_5H_{11}$ | 2.5 | 1.5 | 40 | 65 | 72 | 135 | C | 76.8 | 77.0 |
|  |  |  |  |  |  |  |  |  | H | 9.3 | 9.4 |
| 19 | F | $C_7H_{15}$ | 2.8 | 1.7 | 42 | 47 | 72 | 129 | C | 77.5 | 77.6 |
|  |  |  |  |  |  |  |  |  | H | 9.7 | 9.8 |
| 20 | Cl | $C_5H_{11}$ | 2.5 | 2.2 | 56 | 69 | 73 | 106 | C | 74.0 | 73.7 |
|  |  |  |  |  |  |  |  |  | H | 9.1 | 9.0 |
|  |  |  |  |  |  |  |  |  | Cl | 9.0 | 9.1 | pyridine (50 ml), followed by sufficient agitation, standing overnight, adding toluene (100 ml), extractions with 6N HCl and then with 2N solution of sodium hydroxide and washings with water until the toluene layer became neutral. Toluene was distilled off under reduced pressure and an oily substance as residue was twice recrystallized from ethanol to obtain the objective 4-fluorobenzoic acid trans-4'-(trans-4"-pentylcyclohexyl)cyclohexyl ester (1.4 g) (yield: 37%). This product became a smectic liquid crystal at a m.p. of 60° C. (C-Sm point), became a nematic liquid crystal at 85° C. (Sm-N point), and further became a transparent liquid at 181° C. (N-I point). Further its elemental analysis values almost accorded with its calculated values as shown in Table 2.

EXAMPLES 12-15

Other compounds of the formula (III) were obtained as in Example 11. Their yields, physical properties, etc. are shown together with the results of Example 11 in Table 2.

EXAMPLE 21

Preparation of 4-cyanobenzoic acid trans-4'-(trans-4"-heptylcyclohexyl)cyclohexyl ester (a compound of the formula (VI) wherein R'=$C_7H_{15}$)

Thionyl chloride (20 ml) is added to 4-cyanobenzoic acid (1.3 g) and the mixture is heated at 70°-80° C. for 5 hours, followed by distilling off excess thionyl chloride under reduced pressure. On the other hand, trans-4-(trans-4'-heptylcyclohexyl)cyclohexanol (2 g) is dissolved in a mixed liquid of pyridine (1 ml) with toluene (50 ml), and the solution is added to the benzoyl chloride obtained above, at room temperature. The resulting reaction liquid is allowed to stand overnight, followed by pouring it into water (50 ml), separating the toluene layer, washing with 6N hydrochloric acid and then with 2N aqueous solution of sodium hydroxide, washing with water until the toluene layer becomes neutral, drying over anhydrous sodium sulfate, distilling off toluene under reduced pressure, and recrystallizying the residual solid from ethanol to obtain the objective 4-cyanobenzoic acid trans-4'-(trans-4"-heptylcyclohexyl)cyclohexyl ester (2.3 g). Yield based on trans-4-

TABLE 2

| Example | In formula (III) X | In formula (III) R' | Amount of HO-⬡-⬡-R' used (g) | Yield (g) | Yield (%) | Phase transition points (°C.) C—Sm | Phase transition points (°C.) Sm—N | Phase transition points (°C.) N—I | | Elemental analysis values Analytical values | Elemental analysis values Calculated values |
|---|---|---|---|---|---|---|---|---|---|---|---|
| 12 | F | $C_3H_7$ | 2.2 | 1.3 | 38 | 76 | 87 | 180 | C | 76.1 | 76.3 |
|  |  |  |  |  |  |  |  |  | H | 8.8 | 9.0 |
| 13 | F | $C_4H_9$ | 2.4 | 1.4 | 39 | 52 | 68 | 178 | C | 76.7 | 76.6 |
|  |  |  |  |  |  |  |  |  | H | 9.1 | 9.2 |
| 11 | F | $C_5H_{11}$ | 2.5 | 1.4 | 37 | 60 | 85 | 181 | C | 77.3 | 77.0 |
|  |  |  |  |  |  |  |  |  | H | 9.2 | 9.4 |
| 14 | F | $C_7H_{15}$ | 2.8 | 1.7 | 42 | 68 | 81 | 163 | C | 77.8 | 77.6 |
|  |  |  |  |  |  |  |  |  | H | 9.8 | 9.8 |
| 15 | Cl | $C_5H_{11}$ | 2.5 | 2.1 | 54 | 66 | 70 | 206 | C | 73.6 | 73.7 |
|  |  |  |  |  |  |  |  |  | H | 9.0 | 9.0 |
|  |  |  |  |  |  |  |  |  | Cl | 9.1 | 9.1 |

(trans-4'-heptylcyclohexyl)cycohexanol: 78.8%. This product exhibited a nematic liquid crystal phase, and its C-N point and N-I point were 129.5°–130.3° C. and 213.1°–213.6° C., respectively.

EXAMPLES 22-25

Compounds of the formula (VI) having alkyl groups whose carbon numbers are differrent from that of the compound of Example 21 were prepared as in Example 21. The results are shown together with those of Example 21 in Table 4.

TABLE 4

| Ex-ample | R' in formula (VI) | Yield (g) | Yield (%) | Phase transition points (°C.) C-N point | Phase transition points (°C.) N-I point |
|---|---|---|---|---|---|
| 21 | $C_3H_7$ | 2.10 | 66.7 | 135.7~137.1 | 230.2~231.2 |
| 22 | $C_4H_9$ | 2.05 | 66.5 | 137.6~138.6 | 214.6~215.5 |
| 23 | $C_5H_{11}$ | 2.00 | 66.2 | 134.0~135.2 | 220.5~222.1 |
| 24 | $C_6H_{13}$ | 2.12 | 71.4 | 123.5~125.3 | 205.8~206.9 |
| 25 | $C_7H_{15}$ | 2.30 | 78.8 | 129.5~130.3 | 213.1~213.6 |

EXAMPLE 26

Preparation of 4-cyanobenzoic acid trans-4'-(4''-propylphenyl)cyclohexyl ester (a compound of the formula (VI) wherein $R'=C_3H_7$)

4-Propyl-4'-hydroxybiphenyl (200 g) is dissolved in ethanol (0.5 l) and a commercially available Raney nickel catalyst (20 g) is added, followed by hydrogenation in an autoclave at 80°–120° C. under a hydrogen pressure of 30–40 Kg/cm$^2$G. The reaction is traced by gas chromatography (column: SIDC-560, 10%, 2 m, 250° C.) and stopped when the raw material is extinct. The catalyst is filtered off from the hydrogenation product and ethanol is distilled off under reduced pressure, followed by dissolving it in toluene (200 ml). On the other hand, metallic sodium (23 g) is added to toluene (400 ml) and heated to 110° C., followed by quenching under a high speed agitation to obtain a sodium dispersion, which is then cooled down to room temperature, followed by adding the above toluene solution of the hydrogenation product, stirring at room temperature for one hour, further stirring at 100° C. for 4 hours, cooling and gradually adding methanol (200 ml). The whole is transferred into a separating funnel and washed twice with 10% hydrochloric acid (200 ml) and then once with a saturated aqueous solution of sodium hydrogen carbonate, followed by washing with water until the water layers becomes neutral. The toluene layer is dried over anhydrous sodium sulfate, and toluene is then distilled off under reduced pressure, followed by adding methanol (100 ml) and standing overnight to obtain crystals of trans-4-(4'-propylphenyl)cyclohexanol. Yield: 35.5 g (17.3%). M.p.: 78.2°–80.0° C.

On the other hand, thionyl chloride (20 ml) is added to 4-cyanobenzoic acid (1.5 g) and the mixture is heated at 70°–80° C. for 5 hours, followed by distilling off excess thionyl chloride under reduced pressure. To the residue is added a mixed liquid obtained by dissolving trans-4-(4'-propylphenyl)cyclohexanol obtained above (2 g) in pyridine (1 ml) and toluene (50 ml) at room temperature, followed by vigorous shaking, standing overnight, pouring it into water (50 ml), separating the resulting toluene layer, which is then washed with 6N hydrochloric acid and then with 2N aqueous solution of sodium hydroxide and further with water until the layer becomes neutral, and dried over anhydrous sodium sulfate. Toluene is then distilled off under reduced pressure and the residual solid is recrystallized from ethanol to obtain the objective 4-cyanobenzoic acid trans-4'-(4''-propylphenyl)cyclohexyl ester (2.10 g). Yield based on trans-4-(4'-propylphenyl)cyclohexanol: 66.0%. This product exhibited a nematic liquid crystal phase, and its C-I point and N-I point were 134.5°–136.1° C. and 193.3°–194.5° C., respectively.

EXAMPLES 27-30

Compounds of the formula (V) having alkyl groups whose carbon numbers are different from those of the compound of Example 26 were prepared as in Example 26. The results are shown together with those of Example 26 in Table 5.

TABLE 5

| Ex-ample | R' in formula (V) | Yield (g) | Yield (%) | Phase transition points (°C.) C-N point | Phase transition points (°C.) N-I point |
|---|---|---|---|---|---|
| 26 | $C_3H_7$ | 2.10 | 66.0 | 134.5~136.1 | 193.3~194.5 |
| 27 | $C_4H_9$ | 2.23 | 71.7 | 134.3~134.8 | 181.8~182.2 |
| 28 | $C_5H_{11}$ | 2.37 | 77.7 | 140.9~141.8 | 178.7~179.4 |
| 29 | $C_6H_{13}$ | 2.20 | 73.5 | 131.0~131.8 | 165.0~165.4 |
| 30 | $C_7H_{15}$ | 2.62 | 89.1 | 111.2~113.3 | 163.7~165.5 |

EXAMPLE 31

Preparation of trans-4-acetyloxy-(trans-4'-propylcyclohexyl)cyclohexane (a compound of the formula (VIII) wherein $R=CH_3$ and $R'=C_3H_7$).

Trans-4'-propylcyclohexylcyclohexanol (2.2 g) (0.01 mol) is dissolved in pyridine (10 ml) and acetyl chloride (0.9 g) (0.012 mol) is added at room temperature, followed by sufficient shaking, standing overnight, pouring the resulting material into water (50 ml) and extracting the resulting oily substance with toluene (100 ml). The toluene layer is washed with 6N hydrochloric acid and then with 2 N solution of sodium hydroxide and further with water until the layer becomes neutral, followed by drying over anhydrous sodium sulfate, distilling off toluene under reduced pressure, and recrystallizing the residual oily substance from a small amount of methanol to obtain the objective trans-4-acetyloxy-(trans-4'-propylcyclohexyl) cyclohexane (1.9 g) (yield: 71%). This product was a smectic liquid crystal (Sm). Its C-Sm point (m.p.) and Sm-I point (transparent point) were 48.5° C. and 89.8° C., respectively.

EXAMPLE 32-39

Compounds of the formula (VII) shown in Table 6 were obtained as in Example 31. Their physical properties, etc. are shown together with those of Example 31 in Table 6.

TABLE 6

| Example | In formula (VII) R | In formula (VII) R' | Yield (g) | Yield (%) | Phase transition point (°C.) C-Sm point | Phase transition point (°C.) Sm-I point |
|---|---|---|---|---|---|---|
| 31 | $CH_3$ | $C_3H_7$ | 1.9 | 71 | 48.5 | 89.8 |
| 32 | $CH_3$ | $C_4H_9$ | 2.3 | 82 | 56.4 | 62.0 |
| 33 | $CH_3$ | $C_5H_{11}$ | 2.4 | 82 | 57.4 | 74.4 |
| 34 | $CH_3$ | $C_7H_{15}$ | 2.9 | 90 | 64.0 | 76.5 |
| 35 | $C_2H_5$ | $C_4H_9$ | 2.0 | 68 | 40.9 | 79.5 |
| 36 | $C_2H_5$ | $C_5H_{11}$ | 2.2 | 71 | 38.7 | 89.2 |
| 37 | $C_2H_5$ | $C_7H_{15}$ | 2.5 | 74 | 53.2 | 88.7 |
| 38 | $C_4H_9O$ | $C_5H_{11}$ | 2.1 | 60 | 36.1 | 74.4 |

TABLE 6-continued

| | In formula (VII) | | Yield | | Phase transition point (°C.) | |
|---|---|---|---|---|---|---|
| Example | R | R' | (g) | (%) | C-Sm point | Sm-I point |
| 39 | $C_2H_5O$ | $C_7H_{15}$ | 2.4 | 68 | 47.7 | 92.5 |

EXAMPLE 40

Preparation of trans-4-propylcyclohexanecarboxylic acid trans-4'-(trans-4''-propylcyclohexyl)cyclohexyl ester (a compound of the formula (VIII) wherein $R=C_3H_7$; $R'=C_3H_7$: and $n=1$)

Trans-4-(trans-4'-propylcyclohexyl)cyclohexanol (2.3 g) is dissolved in pyridine (20 ml), and to the solution is added trans-4-propylcyclohexanecarbonyl chloride (1.9 g) prepared in advance, followed by the same procedure as in Example 1, etc. to obtain the objective trans-4-propylcyclohexanecarboxylic acid trans-4'-(trans-4''-propylcyclohexyl) cyclohexyl ester (1.4 g). Yield: 37%. This product exhibited a smectic liquid crystal phase within a broad temperature range and its C-Sm point, Sm-N point and N-I point were 27° C., 194° C. and 201° C., respectively.

EXAMPLES 41 and 42

Example 40 was repeated except that the alkyl group of the raw material of Example 40 was varied, to obtain trans-4-ethylcyclohexanecarboxylic acid trans-4'-(trans-4''-propylcyclohexyl)cyclohexyl ester (yield: 47%, C-Sm point: −15° C., Sm-N point: 186.0° C., N-I point: 186.7° C.) and trans-4-propylcyclohexanecarboxylic acid trans-4'-(trans-4'''-pentylcyclohexyl)cyclohexyl ester (yield: 46%, smectic phase at room temperature, Sm-I point: 211° C.).

EXAMPLE 43

Preparation of trans-4-(trans-4'-propylcyclohexyl)-cyclohexanecarboxylic acid trans-4''(trans-4'''-propylcyclohexyl)cyclohexyl ester (a compound of the formula (VIII) wherein $R=C_3H_7$; $R''=C_3H_7$ and $n=2$)

Trans-4-(trans-4'-propylcyclohexyl)cyclohexanecarbonylic acid (2.5 g) and thionyl chloride (20 ml) are placed in a 100 ml eggplant-type flask, followed by reflux at 80° C. for 5 hours. After completion of the reaction, excess thionyl chloride is distilled off and the residual oily substance, which is trans-4-(trans-4'-propylcyclohexyl)cyclohexanecarbonyl chloride, is then reacted with a solution of trans-4-(trans-4'-propylcyclohexyl)-cyclohexanol (2.2 g) as used in Example 40, in pyridine (20 ml), followed by the same procedure as in Example 40, to obtain the objective trans-4-(trans-4'-propylcyclohexyl)cyclohexanecarboxylic acid trans-4''-(trans-4'''-propylcyclohexyl)cyclohexyl ester (2.2 g) Yield: 48%. This product also is a smectic liquid crystal and its C-Sm point and Sm-I point were 74° C. and 283° C., respectively.

EXAMPLE 44

Preparation of 4-butylbenzoic acid trans-4'-(4''-heptylphenyl)cyclohexyl ester (a compound of the formula (IX) wherein $Y=C_4H_9$ and $R'=C_7H_{15}$)

4-Butylbenzoyl chloride prepared from 4-butylbenzoic acid (1.4 g) and thionyl chloride (6 ml) is reacted with a solution obtained by dissolving trans-4-(4'-heptylphenyl)-cyclohexanol (2 g) in pyridine (1.4 g) and toluene (50 ml), followed by the same procedure as in Example 1, etc. to obtain crystals of the objective 4-butylbenzoic acid trans-4'-(4''-heptylphenyl)cyclohexyl ester. Yield: 2.6 g, 82.3%. Its C-Sm (crystal-smectic transition point), Sm-N point (smectic phase-nematic phase transition point) and N-I (nematic phase-isotropic liquid transition point) were 44.0° C., 67.0° C. and 111.0° C., respectively.

EXAMPLES 45–61

Compounds of the formula (IX) having different substituent groups from those of Example 44 were prepared as in Example 44. Their yields, phase transition points, etc. are shown together with the results of Example 44 in Table 7.

TABLE 7

| | In formula (IX) | | Yield | | Phase transition points (°C.) | | |
|---|---|---|---|---|---|---|---|
| Example | Y | R' | (g) | (%) | C-N or (C-Sm) | Sm-N | N-I |
| 45 | $C_4H_9$ | $C_3H_7$ | 3.0 | 86.5 | 56.0~56.9 | — | 118.2~118.4 |
| 46 | $C_4H_9$ | $C_4H_9$ | 2.7 | 80.0 | 50.0~52.8 | — | 107.0~109.3 |
| 47 | $C_4H_9$ | $C_5H_{11}$ | 2.8 | 84.8 | 60.8~61.5 | — | 117.5~117.8 |
| 48 | $C_4H_9$ | $C_6H_{13}$ | 2.6 | 80.5 | 56.2~56.8 | — | 107.3~107.9 |
| 44 | $C_4H_9$ | $C_7H_{15}$ | 2.6 | 82.3 | 44.0 (C-Sm) | 67.0 | 111.0 |
| 49 | $CH_3O$ | $C_3H_7$ | 3.0 | 92.9 | 78.7~80.3 | — | 177.5~178.0 |
| 50 | $CH_3O$ | $C_5H_{11}$ | 2.5 | 80.9 | 68.5~69.7 | — | 164.8~165.7 |
| 51 | $CH_3O$ | $C_7H_{15}$ | 2.8 | 94.0 | 69.0~69.4 | — | 147.0~147.3 |
| 52 | $C_2H_5O$ | $C_3H_7$ | 2.8 | 83.4 | 87.4~88.0 | — | 183.1~183.4 |
| 53 | $C_2H_5O$ | $C_4H_9$ | 2.2 | 67.2 | 78.6~79.2 | — | 169.8~170.0 |
| 54 | $C_2H_5O$ | $C_5H_{11}$ | 2.2 | 68.7 | 73.2~74.7 | — | 172.4~172.9 |
| 55 | $C_2H_5O$ | $C_6H_{13}$ | 2.3 | 73.3 | 76.0~77.3 | — | 155.3~155.8 |
| 56 | $C_2H_5O$ | $C_7H_{15}$ | 2.5 | 81.2 | 73.0 (C-Sm) | 75.6 | 157.5~158.2 |
| 57 | $C_3H_7O$ | $C_5H_{11}$ | 2.4 | 72.3 | 77.0~77.6 | — | 153.7~154.1 |
| 58 | $C_3H_7O$ | $C_7H_{15}$ | 3.0 | 94.2 | 75.1 (C-Sm) | 76.2 | 142.0~142.4 |
| 59 | $C_4H_9O$ | $C_7H_{15}$ | 2.9 | 88.3 | 81.4 (C-Sm) | 85.5 | 143.4~143.6 |
| 60 | $C_5H_{11}O$ | $C_7H_{15}$ | 2.8 | 82.6 | 69.2 (C-Sm) | 72.4 | 135.4~135.7 |
| 61 | $C_6H_{13}O$ | $C_7H_{15}$ | 3.1 | 88.8 | 82.0 (C-Sm) | 82.7 | 132.6~132.8 |

EXAMPLES 62 and 63

Example 44 was repeated except that trans-4-(4'-propylphenyl)cyclohexanol or trans-4-(4'-hexylphenyl)-cyclohexanol (each 2 g) was used in place of trans-4-(4'-heptylphenyl)cyclohexanol, and 4-(trans-4'-propylcyclohexyl)benzoic acid was used in place of 4-butylbenzoic acid, to prepare 4-(trans-4'-propylcyclohexyl)benzoic acid trans-4"-(4""-propylphenyl)cyclohexyl ester (Example 62) and 4-(trans-4'-propylcyclohexyl)benzoic acid trans-4"-(4"'-hexylphenyl)cyclohexyl ester (Example 63). Their yields, physical properties, etc. are shown in Table 8.

with a mixed liquid obtained by dissolving trans-4-(4'-propylphenyl)-cyclohexanol (2.0 g) in pyridine (1 ml) and toluene (50 ml) to obtain the objective trans-4-propylcyclohexanecarboxylic acid trans-4'-(4"-propylphenyl)cyclohexyl ester (2.20 g). Yield based on trans-4-(4'-propylphenyl)cyclohexanol: 64.8%. Its C-Sm point, Sm-N point and N-I point were 58.4° C., 123.6° C. and 150.6° C., respectively.

TABLE 8

| | In formula (IX) | | Yield | | Phase transition point (°C.) | | |
|---|---|---|---|---|---|---|---|
| Example | Y | R' | (g) | (%) | C—N or (C—Sm) | Sm—N | N—I |
| 62 | 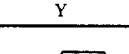 | C$_3$H$_7$ | 3.6 | 88.0 | 123.9~125.3 | — | 220.1~220.7 |
| 63 | 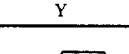 | C$_6$H$_{13}$ | 3.4 | 90.6 | 108.5 (C—Sm) | 132.0~132.8 | 219.5~220.2 |

EXAMPLE 64

Preparation of trans-4-propylcyclohexanecarboxylic acid trans-4'-(4"-propylphenyl)cyclohexyl ester (a compound of the formula (X) wherein Y=C$_3$H$_7$ and R'=C$_3$H$_7$)

Trans-4-propylcyclohexanecarbonyl chloride prepared by reacting trans-4-propylcyclohexanecarboxylic acid (2 g) with thionyl chloride (10 ml) was reacted

EXAMPLES 65–78

Compounds of the formula (X) different from the compound of Example 64 were prepared as in Example 64. Their results are shown together with those of Example 64 in Table 9.

TABLE 9

| | In formula (X) | | Yield | | Phase transition point (°C.) | | N—I or |
|---|---|---|---|---|---|---|---|
| Example | Y | R' | (g) | (%) | C—Sm | Sm—N | Sm—I |
| 65 | C$_2$H$_5$ | C$_3$H$_7$ | 1.90 | 58.2 | 52.1 | 101.6 | 123.9 |
| 66 | C$_2$H$_5$ | C$_4$H$_9$ | 1.65 | 51.7 | 59.1 | 109.3 | 112.4 |
| 64 | C$_3$H$_7$ | C$_3$H$_7$ | 2.20 | 64.8 | 58.4 | 123.6 | 150.6 |
| 67 | C$_3$H$_7$ | C$_4$H$_9$ | 2.02 | 61.0 | 69.1 | 129.1 | 137.2 |
| 68 | C$_3$H$_7$ | C$_5$H$_{11}$ | 2.10 | 64.9 | 50.2 | 130.6 | 139.7 |
| 69 | C$_3$H$_7$ | C$_6$H$_{13}$ | 2.02 | 56.9 | 57.4 | — | 132.1 |
| 70 | C$_3$H$_7$ | C$_7$H$_{15}$ | 2.15 | 58.5 | 32.0 | — | 139.2 |
| 71 | C$_4$H$_9$ | C$_4$H$_9$ | 1.96 | 57.1 | 38.1 | — | 141.6 |
| 72 | C$_5$H$_{11}$ | C$_4$H$_9$ | 2.00 | 56.3 | <30 | — | 147.0 |
| 73 |  (C$_2$H$_5$) | C$_4$H$_9$ | 2.36 | 60.5 | <30 | 211.0 | 223.3 |
| 74 |  (C$_2$H$_5$) | C$_6$H$_{13}$ | 2.25 | 60.9 | <30 | 210.1 | 218.5 |
| 75 |  (C$_3$H$_7$) | C$_4$H$_9$ | 2.41 | 60.0 | 51.1 | 204.7 | 228.8 |
| 76 |  (C$_3$H$_7$) | C$_5$H$_{11}$ | 2.67 | 68.4 | 68.4 | 210.1 | 236.4 |
| 77 |  (C$_3$H$_7$) | C$_6$H$_{13}$ | 2.13 | 56.1 | 32.7 | 202.4 | 239.1 |

TABLE 9-continued

| Example | In formula (X) Y | R' | Yield (g) | Yield (%) | Phase transition point (°C.) C—Sm | Phase transition point (°C.) Sm—N | N—I or Sm—I |
|---|---|---|---|---|---|---|---|
| 78 | C₃H₇—◯— | C₇H₁₅ | 2.59 | 69.8 | <30 | 212.2 | 232.8 |

EXAMPLE 79 (Use example 1)

A liquid crystal composition consisting of:
trans-4-propyl-(4'-cyanophenyl)cyclohexane—24%,
trans-4-pentyl-(4'-cyanophenyl)cyclohexane—36%,
trans-4-heptyl-(4'-cyanophenyl)cyclohexane—25%, and
trans-4-pentyl-(4'-cyanobiphenylyl-4)cyclohexane 15%, has a N-I point of 72.8° C., a αε of +11.1, a threshold voltage of 1.80 V, a saturation voltage of 2.45 V and a viscosity at 20° C. of 30 cp.

In the above blend, trans-4-pentyl(4'-cyanobiphenyl-4)cyclohexane (15%) was replaced by 4-fluorobenzoic acid trans-4'-(trans-4"-propylcyclohexyl)cyclohexyl ester of Example 12 (7.5%) and 4-fluorobenzoic acid trans-4'-(trans-4"-heptylcyclohexyl)cyclohexyl ester of Example 14 (7.5%). The resulting liquid crystal composition had a N-I point of 64.5° C., a Δε of +10.0, a threshold voltage of 1.70 V, a saturation voltage of 2.30 V and a viscosity at 20° C. of 26 cp. The Δε was reduced, and nevertheless the threshold voltage and the saturation voltage were both lowered, and the viscosity was also lowered.

EXAMPLE 80 (Use example 2)

A liquid crystal composition consisting of:
trans-4-propyl(4'-cyanophenyl)cyclohexane—25%,
trans-4-pentyl(4'-cyanophenyl)cyclohexane—38%,
trans-4-heptyl(4'-cyanophenyl)cyclohexane—27%, and
4-fluorobenzoic acid trans-4'-(trans-4"-pentylcyclohexyl)cyclohexyl ester of Example 11—10%, had a N-I point of 83° C., a Δε of +10.7, a threshold voltage of 1.80 V, a saturation voltage of 2.40 V and a viscosity at 20° C. of 29 cp; hence it has superior practical properties. A composition wherein the compound of the present invention was excluded from the above components had a N-I point of 52° C.

EXAMPLE 81 (Use example 3)

A liquid crystal composition A consisting of:
trans-4-propyl-(4'-cyanophenyl)cyclohexane—28%,
trans-4-pentyl-(4'-cyanophenyl)cyclohexane—43%, and
trans-4-heptyl-(4'-cyanophenyl)cyclohexane—29%, had a nematic temperature range of −3°∼+52° C., a dielectric anisotropy value of +10.5, a threshold voltage of 1.53 V in a TN cell, a saturation voltage of 2.12 V and a viscosity at 20° C. of 23 cp.

To this liquid crystal composition (85 parts by weight) were added:
3-fluorobenzoic acid trans-4'-(trans-4"-propylcyclohexyl)cyclohexyl ester of Example 16—7.5 parts, and
3-fluorobenzoic acid trans-4'-(trans-4"-pentylcyclohexyl)cyclohexyl ester of Example 18—7.5 parts.

The resulting liquid crystal mixture had a N-I point of 64° C. (raised), a viscosity at 20° C. of 25 cp, a Δε of +9.0, a threshold voltage of 1.75 V in a TN cell and a saturation voltage of 2.35 V.

EXAMPLE 82 (Use example 4)

To the liquid crystal composition A used in Example 81 (90 parts) were added:
4-cyanobenzoic acid trans-4'-(trans-4"-propylcyclohexyl)cyclohexyl ester of Example 21—5 parts, and
4-cyanobenzoic acid trans-4'-(trans-4"-pentylcyclohexyl)cyclohexyl ester of Example 23—5 parts.

The resulting liquid crystal composition had a N-I point of 66.9° C. (raised), a dielectric anisotropy value Δε of +10.9, a viscosity at 20° C. of 29.9 cp and a threshold voltage of 1.87 V in a TN cell.

Example 83 (Use example 5)

To the liquid crystal composition A (90 parts) were added:
4-cyanobenzoic acid trans-4'-(4"-propylphenyl)cyclohexyl ester of Example 26—5 parts, and
4-cyanobenzoic acid trans-4'-(4"-pentylphenyl)cyclohexyl ester of Example 28—5 parts.

The resulting liquid crystal composition had a N-I point of 60° C. (raised), a dielectric anisotropy Δε of +11.0, a viscosity at 20° C. of 30.5 cp and a threshold voltage of 1.76 V in a TN cell.

EXAMPLE 84 (Use example 6)

To the liquid crystal composition A (75 parts) were added
trans-4-acetyloxy-(trans-4'-heptylcyclohexyl)-cyclohexane of Example 34—13 parts, and
trans-4-propionyloxy-(trans-4'-heptylcyclohexyl)cyclohexane of Example 37—6 parts.

The resulting liquid crystal composition had a nematic liquid crystal temperature range of −10°−+53° C. (broadened), a dielectric anisotropy value Δε of +8.0, a threshold voltage of 1.62 V, a saturation voltage of 2.25 V and a viscosity at 20° C. of 24 cp (almost unchanged).

EXAMPLE 85 (Use example 7)

To the liquid crystal composition A (85 parts) was added trans-4-propylcyclohexanecarboxylic acid trans-4'-(trans-4"-propylcyclohexyl)cyclohexyl ester (15 parts).

The resulting liquid crystal composition had a N-I point of 68° C. (raised), a viscosity at 20° C. of 24 cp (almost unchanged), a Δε of +9.4, a threshold voltage of 1.80 V in a TN cell and a saturation voltage of 2.5 V.

Example 86 (Use example 8)

To the liquid crystal composition A (80 parts) were added
4-butylbenzoic acid trans-4'-(4''-heptylphenyl)-cyclohexyl ester of Example 44—10 parts, and
4-butylbenzoic acid trans-4'-(4''-butylphenyl)-cyclohexyl ester of Example 46—10 parts.

The resulting liquid crystal composition had a nematic temperature range of −10°−+54.5° C. (broadened), a dielectric anisotropy value of +9.0, a threshold voltage of 1.72 V, a saturation voltage of 2.40 V, and a viscosity at 20° C. of 30 cp.

EXAMPLE 87 (Use example 9)

To the liquid crystal composition A (85 parts) was added 4-ethoxybenzoic acid trans-4'-(4''-butylphenyl)-cyclohexyl ester of Example 53 (1.5 part). The resulting liquid crystal composition had a nematic temperature range of −5°−+59.4° C. (broadened), a dielectric anisotropy value of +9.7, a threshold voltage of 1.80 V, a saturation voltage of 2.50 V and a viscosity at 20° C. of 29 cp.

Example 88 (Use example 11)

To the liquid crystal composition A (85 parts) was added trans-4-propylcyclohexanecarboxylic acid trans-4'-(4''-butylphenyl)cyclohexyl ester of Example 67 (15 parts). The resulting liquid crystal mixture had a nematic temperature range of −10°−+56.5° C., a dielectric anisotropy value of +9.2, a threshold voltage value of 1.72 V in a TN cell, a saturation voltage of 2.42 V and a viscosity at 20° C. of 26 cp. It is seen that the compound of the present invention is effective for broadening the nematic temperature range without substantially raising the viscosity.

What is claimed is:

1. A carboxylic acid cyclohexyl ester derivative expressed by the formula

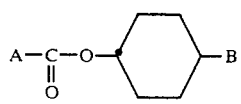
(I)

wherein A represents

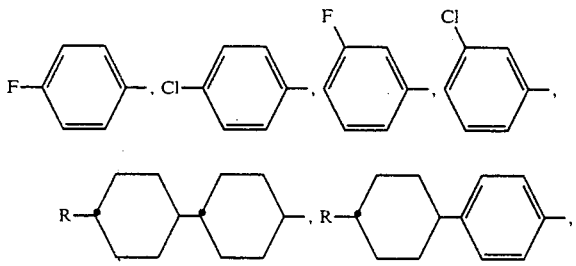

B represents

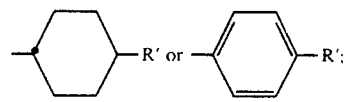

R represents an alkyl group or an alkoxy group, both having 1 to 10 carbon atoms; and R' represents an alkyl group having 1 to 10 carbon atoms.

2. A compound according to claim 1, expressed by the formula

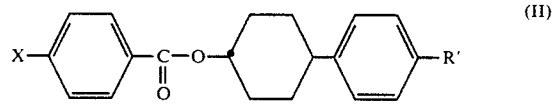
(II)

wherein X represents F or Cl and R' represents an alkyl group of 1 to 10 carbon atoms.

3. A compound according to claim 1, expressed by the formula

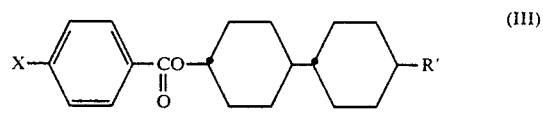
(III)

wherein X represents F or Cl and R' represents an alkyl group of 1 to 10 carbon atoms.

4. A compound according to claim 1, expressed by the formula

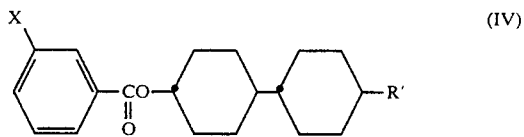
(IV)

wherein X represents F or Cl and R' represents an alkyl group of 1 to 10 carbon atoms.

5. A compound according to claim 1, expressed by the formula

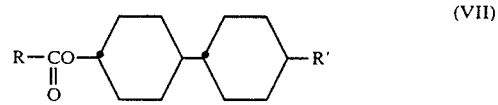
(VII)

wherein R represents an alkyl group or an alkoxy group, both having 1 to 10 carbon atoms, and R' represents an alkyl group of 1 to 1 carbon atoms.

6. A compound according to claim 1, expressed by the formula

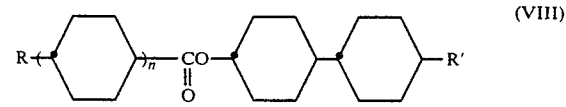
(VIII)

wherein R and R' both represent an alkyl group of 1 to 10 carbon atoms and n represents 2.

* * * * *